US011041869B2

(12) United States Patent
Sato et al.

(10) Patent No.: US 11,041,869 B2
(45) Date of Patent: *Jun. 22, 2021

(54) METHOD AND REAGENT FOR QUANTIFYING CHOLESTEROL IN HIGH DENSITY LIPOPROTEIN 3

(71) Applicant: DENKA COMPANY LIMITED, Tokyo (JP)

(72) Inventors: Noriyuki Sato, Gosen (JP); Yasuki Itoh, Gosen (JP)

(73) Assignee: DENKA COMPANY LIMITED, Tokyo (JP)

( * ) Notice: Subject to any disclaimer, the term of this patent is extended or adjusted under 35 U.S.C. 154(b) by 27 days.

This patent is subject to a terminal disclaimer.

(21) Appl. No.: 14/906,589

(22) PCT Filed: Jul. 24, 2014

(86) PCT No.: PCT/JP2014/069513
§ 371 (c)(1),
(2) Date: Jan. 21, 2016

(87) PCT Pub. No.: WO2015/012334
PCT Pub. Date: Jan. 29, 2015

(65) Prior Publication Data
US 2016/0161512 A1 Jun. 9, 2016

(30) Foreign Application Priority Data
Jul. 24, 2013 (JP) .............................. JP2013-153294

(51) Int. Cl.
G01N 33/92 (2006.01)
C12Q 1/60 (2006.01)
C07C 43/20 (2006.01)
C07C 43/215 (2006.01)

(52) U.S. Cl.
CPC ............. G01N 33/92 (2013.01); C07C 43/20 (2013.01); C07C 43/215 (2013.01); C12Q 1/60 (2013.01); G01N 2405/00 (2013.01)

(58) Field of Classification Search
None
See application file for complete search history.

(56) References Cited

U.S. PATENT DOCUMENTS 7,348,158 B2 * 3/2008 Matsui .................... C12Q 1/60
435/11
8,765,394 B2 * 7/2014 Matsui .................... C12Q 1/60
435/11
9,151,768 B2 * 10/2015 Higuchi ................. G01N 33/92
2013/0157374 A1 * 6/2013 Higuchi ................. G01N 33/92
436/71
2013/0164769 A1 * 6/2013 Higuchi .................... C12Q 1/60
435/11
2013/0171674 A1 * 7/2013 Higuchi .................... C12Q 1/44
435/11

FOREIGN PATENT DOCUMENTS

| EP | 0 877 422 A1 | 12/1998 | |
| EP | 1 580 279 A1 | 9/2005 | |
| EP | 1 854 894 A1 | 11/2007 | |
| EP | 2 597 158 A1 | 5/2013 | |
| EP | 2 607 901 A1 | 6/2013 | |
| JP | 2001-346598 A | 12/2001 | |
| JP | 2009-207463 A | 9/2009 | |
| WO | WO 2012/011554 | * 1/2012 | ............... C12Q 1/60 |
| WO | WO 2012/011556 | * 1/2012 | ............. G01N 33/92 |
| WO | WO 2012/011563 | * 1/2012 | ............. G01N 33/92 |
| WO | WO 2013/111820 A1 | 8/2013 | |

OTHER PUBLICATIONS

WO-2012-011554—english, English translation of the Japanese WIPO document WO 2012/011554.*
WO2012011556—english, English translation of the Japanese WIPO document WO 2012/011556.*
WO2012011563—english, English translation of the Japanese WIPO document WO 2012/011563.*
Ahmadraji, T. and A. J. Killard, "The evolution of selective analyses of HDL and LDL cholesterol in clinical and point of care testing," Analytical Methods (Aug. 7, 2013), vol. 5, No. 15, pp. 3603-3762.
Extended European European Search Report dated Jan. 25, 2017, in European Patent Application No. 14829002.6.
Ito et al., "Development of a homogeneous assay for measurement of high-density lipoprotein-subclass cholesterol," Clinica Chimica Acta (2014), vol. 427, pp. 86-93.
Okada et al., "Directed Measurement of HDL Cholesterol: Method Eliminating Apolipoprotein E-Rich Particles," Journal of Clinical Laboratory Analysis (2001), vol. 15, pp. 223-229.

* cited by examiner

Primary Examiner — Robert J Yamasaki
(74) Attorney, Agent, or Firm — Birch, Stewart, Kolasch & Birch, LLP

(57) ABSTRACT

Disclosed are a method and a reagent for quantifying HDL3 in a test sample without requiring laborious operations. The method for quantifying cholesterol in high-density lipoprotein 3 comprises reacting a test sample with one or more surfactants which react specifically with high-density lipoprotein 3, and quantifying cholesterol. When one surfactant is used, the surfactant is one selected from the group consisting of polyoxyethylene polycyclic phenyl ethers having an HLB of 12.5 to 15. When two or more surfactants are used, at least one of the surfactants is at least one selected from the group consisting of polyoxyethylene polycyclic phenyl ethers, and the two or more surfactants are combined so as to provide the total HLB of 12.5 to 15 of the combined surfactants.

5 Claims, 3 Drawing Sheets

METHOD AND REAGENT FOR QUANTIFYING CHOLESTEROL IN HIGH DENSITY LIPOPROTEIN 3

TECHNICAL FIELD

The present invention relates to a method and a reagent for quantifying cholesterol in high-density lipoprotein 3 (which may be hereinafter referred to as "HDL3") (cholesterol in HDL3 may be hereinafter referred to as "HDL3 cholesterol" or "HDL3-C").

BACKGROUND ART

Since high-density lipoprotein (HDL) cholesterol receives cholesterol from various tissues including walls of blood vessels with arteriosclerosis, it is involved in the action of efflux of cholesterol accumulated in cells. Therefore, HDL cholesterol is also called the reverse cholesterol transport system. High-density lipoprotein is known to have negative correlation with arteriosclerotic diseases such as coronary arteriosclerosis. Accordingly, an HDL value lower than a predetermined lower limit is regarded as an indication of hyperlipidemia, and the value is known to be useful as an index of arteriosclerosis.

HDL is constituted by apoprotein, phospholipid, cholesterol and triglyceride. HDL has a specific gravity of d=1.063 to 1.210 g/mL, and can be divided into two fractions, that is, HDL2, wherein d=1.063 to 1.125 g/mL, and HDL3, wherein d=1.125 to 1.210 g/mL. A notch is found at the portion of d=1.125 in the distribution curve of lipoprotein, and the part having higher specific gravities in the curve corresponds to HDL3. Alternatively, HDL can be divided into subfractions based on the content of apolipoprotein E among the apoproteins in HDL, wherein HDLs having higher contents of apoE are defined as apoE-rich HDLs.

HDL is known to function not only as a whole as usual but also as the individual HDL2 and HDL3 subfractions having different functions. It is clinically known that CETP deficiency prevents metabolism of HDL to LDL or IDL, leading to an increase in the HDL cholesterol level. The HDL increased by CETP deficiency is HDL2. HDL2 is said to have an antiarteriosclerotic action. It is also said that CETP deficiency causes an increase in apoE-rich HDL, and that, since apo-E-rich HDL has a strong cholesterol-efflux ability and antiplatelet action, it is a better HDL among HDLs. Further, a decrease in the lecithin-cholesterol acyl transferase (LCAT) activity prevents conversion of HDL3 to HDL2, resulting in an increase in HDL3. It is suggested that increased HDL3 leads to increased incidence rates of coronary artery diseases. In view of such tendencies, it is expected that measurement of each of the HDL subfractions may contribute to judgment of whether or not a patient is suffering from arteriosclerosis, and of the cause of the disease. Further, at present, in view of these functions of HDL subfractions, manufacturers are developing therapeutic agents that inhibit the function of CETP, decrease the LDL cholesterol level, and increase the HDL cholesterol level.

Establishment of a simple method for measuring the HDL subfractions may lead to detailed elucidation of their functions, and to their therapeutic effects in the future.

Examples of the methods for measuring HDL subfractions that are known at present include ultracentrifugation, high-performance liquid chromatography (HPLC), HDL3 precipitation (Patent Document 1) and NMR.

In ultracentrifugation, fractionation is carried out utilizing the difference in the specific gravity of lipoprotein. This method has drawbacks in that the operation requires a skill; the method takes many days; and the cost is high. In the method by Okazaki et al. wherein HPLC is used for separating HDL2 and HDL3, the operation takes a long time, and special equipment is required. HDL3 precipitation is a method wherein a reagent containing a divalent metal ion and dextran sulfate is used to aggregate lipoproteins other than HDL3, and HDL3 in the supernatant portion is recovered by centrifugation and measured using an automatic analyzer. This method is not widely used since the method has drawbacks in that the operation of this method also requires a skill; the method is a manual method; the method requires an operation of sample pretreatment; and a certain length of time is required before measurement. Further, NMR, which is a method wherein the number of particles of lipoprotein is measured by nuclear magnetic resonance, is not commonly employed since the method requires special equipment.

There is a method for analyzing HDL subfractions (Patent Document 2). Although this method enables measurement with a general purpose automatic apparatus, the method employs a method wherein a surfactant is used to prevent an enzyme from acting on lipoproteins other than HDL3. Therefore, since the HDL3 reaction is allowed to proceed in the presence of the lipoproteins other than the lipoprotein of interest, the measurement might be influenced by such lipoproteins or, in cases where the prevention is not sufficient, the lipoproteins other than HDL3 might be undesirably measured together.

Thus, as an alternative to the above methods, a reagent that enables simple and more selective quantification of cholesterol needs to be invented.

PRIOR ART DOCUMENTS

Patent Documents

[Patent Document 1] JP 2009-207463 A
[Patent Document 2] JP 2001-346598 A

SUMMARY OF THE INVENTION

Problems to be Solved by the Invention

An object of the present invention is to provide a method and a reagent for quantifying HDL3 in a test sample without requiring laborious operations.

Means For Solving the Problems

As a result of intensive study, the present inventors found a surfactant(s) which react(s) specifically with HDL3. The present inventors also inferred that HDL3 cholesterol in a test sample can be quantified by reacting such surfactant(s) with the test sample and quantifying cholesterol, and this was then experimentally confirmed to be possible, thereby completing the present invention.

That is, the present invention provides a method for quantifying cholesterol in high-density lipoprotein 3, the method comprising reacting a test sample with one or more surfactants which react specifically with high-density lipoprotein 3 and quantifying cholesterol; wherein when one surfactant is used, the surfactant is one selected from the group consisting of polyoxyethylene polycyclic phenyl ethers having an HLB of 12.5 to 15; and when two or more surfactants are used, at least one of the surfactants is at least one selected from the group consisting of polyoxyethylene polycyclic phenyl ethers, and the two or more surfactants are combined so as to provide the total HLB of 12.5 to 15 of the combined surfactants. The present invention also provides a reagent for quantifying cholesterol in high-density lipoprotein 3, the reagent comprising one or more surfactants which react specifically with high-density lipoprotein 3; wherein when one surfactant is used, the surfactant is one selected from the group consisting of polyoxyethylene polycyclic phenyl ethers having an HLB of 12.5 to 15; and when two or more surfactants are used, at least one of the surfactants is at least one selected from the group consisting of polyoxyethylene polycyclic phenyl ethers, and the two or more surfactants are combined so as to provide the total HLB of 12.5 to 15 of the combined surfactants. Further, the present invention provides a use of the reagent according to the above-described present invention for quantifying cholesterol in high-density lipoprotein 3.

Effect of the Invention

By the present invention, HDL3 cholesterol in a test sample can be specifically quantified with an automatic analyzer without requiring laborious operations such as ultracentrifugation or pretreatment. Further, quantification of the HDL2 cholesterol level can also be carried out by subtracting the HDL3 cholesterol level from the total HDL cholesterol level obtained by a conventional method for quantifying the total HDL cholesterol in a test sample.

MODE FOR CARRYING OUT THE INVENTION

Figure 1:
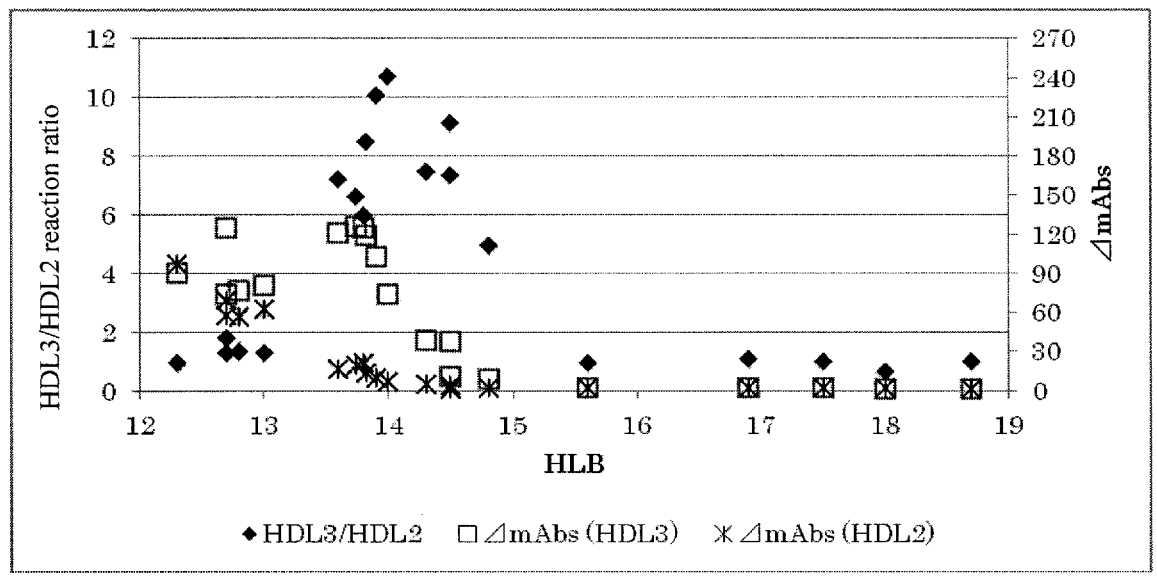
FIG. 1 shows the relationship between the HLB of various polyoxyethylene polycyclic phenyl ethers including polyoxyethylene styrenated phenylethers and HDL3/HDL2 reaction ratio, which comparison was carried out in Example 3.

The test sample to be subjected to the method of the present invention is not limited as long as HDL3 cholesterol in the sample is to be quantified. The sample is preferably serum or blood plasma, or a dilution thereof, and serum or a dilution thereof is especially preferred.

When the term "react" is used for a surfactant in the present invention, the term means that the surfactant makes an enzyme act easily on a lipoprotein, or means to protect lipoprotein such that an enzyme cannot act on the lipoprotein.

In the method of the present invention, a surfactant(s) which specifically react(s) with HDL3 (which means that the surfactant hardly reacts with lipoproteins other than HDL3) is(are) reacted with a test sample. The surfactant(s) which specifically react(s) with HDL3 is(are) at least one selected from the group consisting of polyoxyethylene polycyclic phenyl ethers. Among the polyoxyethylene polycyclic phenyl ethers, polyoxyethylene styrenated phenylethers are preferred, and polyoxyethylene distyrenated phenylethers are more preferred.

More specifically, examples of polyoxyethylene polycyclic phenyl ethers include Newcol-610 (Trade name, produced by Nippon Nyukazai Co., Ltd., company names hereinafter represent names of manufacturers, and all names described together with company names hereinafter represent trade names), Newcol-710 (Nippon Nyukazai), ADEKATOL PC-10 (ADEKA), ADEKATOL PC-13 (ADEKA) and ADEKATOL SP-12 (ADEKA). Among the polyoxyethylene polycyclic phenyl ethers, examples of polyoxyethylene styrenated phenylethers include Emulgen A60 (Kao Corporation), Emulgen A90 (Kao Corporation), BLAUNON DSP-12.5 (AOKI OIL INDUSTRIAL), BLAUNON TSP-16 (AOKI OIL INDUSTRIAL), Noigen EA-137 (Dai-ichi Kogyo Seiyaku), Noigen EA-157 (Dai-ichi Kogyo Seiyaku) and Noigen EA-167 (Dai-ichi Kogyo Seiyaku). Among these, Emulgen A60 (Kao Corporation), Emulgen A90 (Kao Corporation) and Newcol-710 (Nippon Nyukazai) are classified into polyoxyethylene distyrenated phenylethers. Each of these surfactants may be used alone, or two or more types of the surfactants may be used in combination.

The surfactant which reacts specifically with HLD3 preferably has an HLB of 12.5 to 15, more preferably 13.5 to 14.5. Even when one surfactant to be used has an HLB of 12.5 to 15, two or more surfactants including a surfactant(s) not having an HLB of 12.5 to 15 may be used in combination so as to provide the total HLB of 12.5 to 15 of the used surfactants.

The surfactant which reacts specifically with HLD3 preferably has a concentration of 0.025 to 5.0% (w/v), more preferably 0.25 to 2.5% (w/v) in terms of the final concentrations.

In the method of the present invention, cholesterol is quantified by the reaction of the above surfactants. Quantification methods per se of cholesterol are well known, and any of the well-known methods may be used. A concrete description is also given in Examples below. For example, ester-type cholesterol in lipoprotein is hydrolyzed with cholesterol esterase to produce free cholesterol and a fatty acid, and the produced free cholesterol and free cholesterol inherently existing in lipoprotein are converted using cholesterol oxidase to generate cholestenone and hydrogen peroxide. A quinone pigment is then formed in the presence of peroxidase, and quantified. Examples of compounds that generate a quinone pigment include HDAOS (N-(2-hydroxy-3-sulfopropyl)-3,5-dimethoxyaniline), DAOS (N-ethyl-N-(2-hydroxy-3-sulfopropyl)-3,5-dimethoxyaniline sodium salt) or TOOS (N-ethyl-N-(2-hydroxy-3-sulfopropyl)-3-methylaniline sodium salt dihydrate) and 4-aminoantipyrine, but the compounds are not restricted as long as the combination allows generation of a quinone pigment. In cases where cholesterol esterase and cholesterol oxidase are used in the preceding step described later, the cholesterol esterase and cholesterol oxidase used in the preceding step may be used as they are in the step of the present invention (step of reacting an HDL3-specific surfactant), without further addition.

The concentration of the compound for generation of a quinone pigment is, for example, preferably about 0.5 to about 3.0 mmol/L in the case of TOOS, or 0.1 to 8.0 mmol/L in the case of 4-aminoantipyrine. The concentration of peroxidase is preferably 0.4 to 40.0 U/mL.

As the reaction liquid, various buffers used in normal biochemical reactions may be used, and the pH of the reaction liquid is preferably between 5 and 8. The solution is preferably Good's, Tris, phosphate or glycine buffer solution, and is preferably a Good's buffer such as bis(2-hydroxyethyl)iminotris(hydroxyethyl)methane (Bis-Tris), piperazine-1,4-bis(2-ethanesulfonic acid) (PIPES), piperazine-1,4-bis(2-ethanesulfonic acid), sesqui sodium salt monohydrate (PIPES 1.5Na), 2-hydroxy-3-morpholinopropanesulfonic acid (MOPSO), N,N-bis(2-hydroxyethyl)-2-aminoethanesulfonic acid (BES), 2-[4-(2-hydroxyethyl)-1-piperazinyl]ethanesulfonic acid (HEPES) or piperazine-1,4-bis(2-hydroxy-3-propanesulfonic acid) (POPSO).

The reaction temperature is preferably about 25 to about 40° C., more preferably 35 to 38° C., most preferably 37° C. The reaction time is not restricted, and is usually about 2 to about 10 minutes.

The method of the present invention can also be carried out by directly reacting the above surfactant with the test sample, but is preferably carried out by first performing the preceding step for transferring cholesterol in lipoproteins other than HDL or HDL3 to the outside of the reaction system and then subjecting the sample after the preceding step to the method of the present invention, in view of more accurate quantification of HDL3 cholesterol.

The preceding step is preferably carried out in the presence of a surfactant that reacts with lipoproteins other than HDL or a surfactant that reacts with lipoproteins other than HDL3.

Examples of the surfactant that reacts with lipoproteins other than HDL or HDL3 include, but are not limited to, nonionic surfactants such as polyoxyethylene sorbitan derivatives, polyoxyethylene-polyoxypropylene condensates and polyoxyethylene-stearylamine; anionic surfactants such as amide ether sulfate and polyoxyethylene alkyl ether sodium sulfate; amphoteric surfactants such as coconut oil fatty acid-amidopropyldimethyl-aminoacetic acid betaine, alkyl dimethyl-aminoacetic acid betaine and lauryl betaine; and cationic surfactants such as lauryl trimethyl ammonium chloride.

More specifically, Examples of the surfactant that reacts with lipoproteins other than HDL or HDL3 include nonionic surfactants such as polyoxyethylene sorbitan monooleate Nonion OT-221 (NOF Corporation) polyoxyethylene-polyoxypropylene condensate Pluronic F68 (ADEKA), Pluronic F88 (ADEKA), Pluronic F127 (ADEKA), Pluronic P103 (ADEKA), Pluronic P123 (ADEKA) polyoxyethylene-stearylamine Nymeen S210 (NOF Corporation), Emulgen A500 (Kao Corporation); anionic surfactants such as amide ether sulfate Sunamide CF-10 (NOF Corporation), polyoxyethylene alkyl ether sodium sulfate Levenol WX (Kao Corporation); amphoteric surfactants such as coconut oil fatty acid-amidopropyldimethyl-aminoacetic acid betaine Nissan Anon BDF-SF (NOF Corporation), alkyl dimethyl-aminoacetic acid betaine Nissan Anon BF (NOF Corporation) and lauryl betaine Amphitol 24B (Kao Corporation); and cationic surfactants such as lauryl trimethyl ammonium chloride Kohtamin 24P (Kao Corporation). Each of these may be used alone, or two or more types of these may be used in combination.

The concentration of the surfactant to be used in the preceding step is preferably 0.01 to 5.0% (w/v), more preferably about 0.03 to about 3.0% (w/v).

In the preceding step, cholesterol is transferred to the outside of the reaction system by the reaction with the surfactant. The term "transferred to the outside of the reaction system" herein means that cholesterol and esters thereof are eliminated or protected such that the cholesterol and esters thereof are not involved in the later steps.

The term "elimination" herein means that cholesterol of lipoprotein in a test sample is degraded such that the cholesterol does not affect the reaction for measurement of cholesterol in a later step. Examples of the method for eliminating lipoprotein cholesterol include a method wherein cholesterol esterase and cholesterol oxidase are allowed to act on the cholesterol, followed by decomposition of the produced hydrogen peroxide into water and oxygen using catalase. Alternatively, a hydrogen donor may be reacted with the produced hydrogen peroxide using peroxidase to convert the hydrogen peroxide to a colorless quinone. The method for eliminating lipoprotein cholesterol is not restricted to these. The method of elimination of cholesterol per se is well known in the art, and is also described concretely in Examples below.

The term "protection" means to protect lipoprotein in a test sample such that the lipoprotein does not react upon cholesterol measurement in a later step. Examples of the method of protection of lipoprotein include, but are not limited to, a method wherein a surfactant is used to specifically protect each lipoprotein such that cholesterol esterase and cholesterol oxidase do not act on the lipoprotein.

In cases where the preceding step wherein hydrogen peroxide produced in the preceding step is decomposed using catalase is used, a catalase inhibitor sodium azide is used by addition to the reaction liquid in the second step. The concentration of sodium azide in this case is usually about 0.1 g/L to about 1.0 g/L.

The present inventors further discovered that phospholipase and/or sphingomyelinase act on lipoproteins but hardly act on HDL3. Accordingly, by allowing phospholipase and/or sphingomyelinase (these may be hereinafter collectively referred to as the "phospholipase and/or the like") to coexist with the above-described surfactant, HDL3 cholesterol can be more accurately quantified, which is preferred.

The phospholipase is not restricted as long as it acts on phosphatidyl choline. Phospholipase A, phospholipase C and phospholipase D are preferred, and phospholipase C and phospholipase D are especially preferred. The sphingomyelinase is not restricted as long as it acts on sphingomyelin. Since the phospholipase and/or the like are commercially available, commercially available products may be preferably used. Each of the phospholipase and/or the like may be used alone, or two or more types of the phospholipase and the like may be used in combination.

The final concentration of phospholipase and/or the like (the total concentration, in cases where two or more types of phospholipase are used in combination) is preferably about 0.1 to about 100 U/mL, more preferably about 0.2 to about 50 U/mL.

Also in cases where the preceding step is carried out in the presence of a surfactant, the reaction conditions (reaction temperature, time, buffer and the like) are as described above.

In the preceding step, the reaction step by an enzyme and the reaction step by a surfactant can be carried out simultaneously as a single step by simultaneously adding an enzyme system and surfactant for transferring cholesterol to the outside of the reaction system. Different surfactants are used between the first step and the second step.

In cases where cholesterol esterase and cholesterol oxidase are used in the preceding step, the concentration of cholesterol esterase is preferably about 0.1 to about 10.0 U/mL, more preferably about 0.2 to about 3.0 U/mL. The concentration of cholesterol oxidase is preferably about 0.05 to about 10.0 U/mL, more preferably about 0.1 to about 1.0 U/mL. The cholesterol esterase is not restricted as long as it acts on ester-type cholesterol, and examples of the cholesterol esterase which may be used include commercially available products such as cholesterol esterase (CEBP) manufactured by Asahi Kasei Corporation and cholesterol esterase (COE-311, COE-312) manufactured by Toyobo Co., Ltd. Further, the cholesterol oxidase is not restricted as long as it acts on free cholesterol, and examples of the cholesterol oxidase which may be used include commercially available products such as cholesterol oxidase (CONII) manufactured by Asahi Kasei Corporation and cholesterol oxidase (COO-311, COO-321, COO-331) manufactured by Toyobo Co., Ltd.

In cases where peroxidase is used in the preceding step, the concentration of peroxidase is preferably about 2.0 to about 5.0 U/mL, more preferably about 3.0 to about 4.0 U/mL. In cases where a compound for conversion into a colorless quinone is used, the concentration of the compound is preferably about 0.4 to about 0.8 mmol/L.

The other conditions for the preceding step (reaction temperature, reaction time, buffer and the like) may be the same as that for the above-described method of the present invention.

The present invention will now be described more concretely by way of Examples below. However, the present invention is not limited to the Examples below.

EXAMPLES

Example 1

Fractionation was carried out to obtain the HDL2 fraction and the HDL3 fraction as follows. A test sample containing HDL, that is, serum was subjected to ultracentrifugation using a solution with sodium chloride and sodium bromide such that separation occurs at a specific gravity at the border between HDL2 and HDL3 (1.125), and each resulting fraction was collected.

Fractionation by ultracentrifugation was carried out to obtain the CM-VLDL fraction, LDL fraction, HDL2 fraction and HDL3 fraction, and each fraction was reacted with Reagent A described below. Reagent B described below was further added to the reaction solution to perform measurement. In the measurement, 150 μL of Reagent A was added to 2 μL of each fraction, and the reaction was allowed to proceed for 5 minutes with warming, followed by addition of 50 μL of Reagent B to the reaction solution and additional 5 minutes of reaction with warming. The absorbances at a main wavelength of 600 nm and a sub-wavelength of 700 nm were measured.

Reagent A

| | |
|---|---|
| BES buffer (pH 6.6) | 100 mmol/L |
| TOOS | 1.5 mmol/L |
| Pluronic F88 | 0.05 w/v % |
| Catalase | 600 U/mL |
| Cholesterol oxidase | 0.8 U/mL |
| Cholesterol esterase | 2.0 U/mL |
| Sphingomyelinase | 0.5 U/mL |

Reagent B

| | |
|---|---|
| BES buffer (pH 7.0) | 100 mmol/L |
| Sodium azide | 0.1% |
| Various surfactants* | 2.0 w/v % |
| 4-Aminoantipyrine | 4.0 mmol/L |
| Peroxidase | 3.5 U/mL |

*In cases where two or more surfactants are used in combination, the total amount is 2.0 w/v %.

The amount of the change in absorbance of each fraction at a unit time after the addition of Reagent B is shown in Table 1. Specific reaction with HDL3 can be confirmed.

TABLE 1

| | HLB | CM-VLDL | LDL | HDL2 | HDL3 |
|---|---|---|---|---|---|
| Polyoxyethylene polycyclic phenyl ether alone | 13.8 | 1.9 | 1.0 | 13.5 | 38.2 |
| | 13.6 | 0.7 | 1.5 | 9.4 | 30.5 |
| Polyoxyethylene polycyclic phenyl ethers were mixed | 14.1 | 2.9 | 0.8 | 9.8 | 36.0 |
| Polyoxyethylene styrenated phenylethers were mixed | 13.7 | 1.5 | 1.4 | 23.9 | 47.0 |
| Polyoxyethylene distyrenated phenylethers were mixed | 13.7 | 1.4 | 1.5 | 23.9 | 47.8 |

(unit: mAbs)

Example 2

Fractionation by ultracentrifugation was carried out to obtain the CM-VLDL fraction, LDL fraction, HDL2 fraction and HDL3 fraction, and each fraction was reacted with Reagent C described below. Reagent D described below was further added to the reaction solution to perform measurement. In the measurement, 150 μL of Reagent C was added to 2 μL of each fraction, and the reaction was allowed to proceed for 5 minutes with warming, followed by addition of 50 μL of Reagent D to the reaction solution and additional 5 minutes of reaction with warming. The absorbances at a main wavelength of 600 nm and a sub-wavelength of 700 nm were measured.

Reagent C

| | |
|---|---|
| BES buffer (pH 6.6) | 100 mmol/L |
| HDAOS | 0.56 mmol/L |
| Nonion OT-221 | 0.01 w/v % |
| Catalase | 600 U/mL |
| Cholesterol oxidase | 0.8 U/mL |
| Cholesterol esterase | 2.8 U/mL |

Reagent D

| | |
|---|---|
| BES buffer (pH 7.0) | 100 mmol/L |
| Sodium azide | 0.1% |
| Polyoxyethylene polycyclic phenyl ether (HLB: 13.8) | 2.0 w/v % |
| 4-Aminoantipyrine | 4.0 mmol/L |
| Peroxidase | 3.5 U/mL |

The amount of the change in absorbance of each fraction at a unit time after the addition of Reagent D is shown in Table 2. Specific reaction with HDL3 can be confirmed.

TABLE 2

|  | HLB | CM-VLDL | LDL | HDL2 | HDL3 |
|---|---|---|---|---|---|
| Polyoxyethylene polycyclic phenyl ether alone | 13.8 | 0.9 | 2.0 | 1.3 | 50.4 |

(unit: mAbs)

Example 3

Fractionation by ultracentrifugation was carried out to obtain the CM-VLDL fraction, LDL fraction, HDL2 fraction and HDL3 fraction, and each fraction was reacted with Reagent E described below. Reagent F described below was further added to the reaction solution to perform measurement. In the measurement, 150 µL of Reagent E was added to 2 µL of each fraction, and the reaction was allowed to proceed for 5 minutes with warming, followed by addition of 50 µL of Reagent F to the reaction solution and additional 5 minutes of reaction with warming. The absorbances at a main wavelength of 600 nm and a sub-wavelength of 700 nm were measured.

Reagent E

| BES buffer (pH 6.6) | 100 mmol/L |
|---|---|
| TOOS | 1.5 mmol/L |
| Pluronic F88 | 0.05 w/v % |
| Catalase | 1200 U/mL |
| Cholesterol oxidase | 0.3 U/mL |
| Cholesterol esterase | 2.0 U/mL |
| Sphingomyelinase | 0.5 U/mL |

Reagent F

| BES buffer (pH 7.0) | 100 mmol/L |
|---|---|
| Sodium azide | 0.1% |
| Various surfactants* | 2.0 w/v % |
| 4-Aminoantipyrine | 4.0 mmol/L |
| Peroxidase | 30 U/mL |

*In cases where two or more surfactants are used in combination, the total amount is 2.0 w/v %.

The amount of the change in absorbance of each fraction at a unit time after the addition of Reagent F is shown in Table 3, and the HLD3/HLD2 reaction ratio is shown in FIG. 1. It can be seen that high HDL3/HDL2 reaction ratio can be attained at an HLB of 12 to 15, in particular 13.5 to 14.5 of the polyoxyethylene polycyclic phenyl ethers including polyoxyethylene styrenated phenylether.

TABLE 3

|  | HLB | CM-VLDL | LDL | HDL2 | HDL3 |
|---|---|---|---|---|---|
| Polyoxyethylene polycyclic phenyl ether alone | 12.3 | 18.7 | 55.0 | 97.2 | 90.3 |
|  | 12.7 | 6.6 | 14.5 | 58.0 | 73.6 |
|  | 13.6 | 2.9 | 5.0 | 16.8 | 121.4 |
|  | 13.8 | 2.7 | 3.2 | 21.0 | 125.4 |
|  | 14.5 | 1.0 | 1.2 | 4.1 | 37.7 |
| Polyoxyethylene styrenated phenylether alone | 12.7 | 4.8 | 10.9 | 68.9 | 124.5 |
|  | 13.0 | 6.0 | 13.7 | 62.5 | 80.6 |
|  | 14.3 | 1.4 | 1.6 | 5.2 | 38.6 |
|  | 14.8 | 1.2 | 0.2 | 1.8 | 8.7 |

TABLE 3-continued

|  | HLB | CM-VLDL | LDL | HDL2 | HDL3 |
|---|---|---|---|---|---|
|  | 15.6 | 0.8 | 1.1 | 2.2 | 2.1 |
|  | 16.9 | 0.0 | 0.7 | 1.6 | 1.7 |
|  | 17.5 | 0.3 | 0.9 | 1.8 | 1.8 |
|  | 18.7 | 0.7 | 0.3 | 1.5 | 1.5 |
| Polyoxyethylene distyrenated phenylether alone | 12.8 | 6.9 | 13.5 | 56.9 | 76.5 |
|  | 14.5 | 1.0 | 0.8 | 1.5 | 10.9 |
|  | 18.0 | 0.0 | 1.0 | 2.2 | 1.4 |
| Polyoxyethylene distyrenated phenylethers are mixed | 13.7 | 2.2 | 2.9 | 18.9 | 125.6 |
|  | 13.8 | 1.9 | 2.3 | 14.0 | 118.7 |
|  | 13.9 | 1.8 | 1.9 | 10.2 | 102.7 |
|  | 14.0 | 1.0 | 1.6 | 7.0 | 74.5 |

(unit: mAbs)

Example 4

Fractionation by ultracentrifugation was carried out to obtain the CM-VLDL fraction, LDL fraction, HDL2 fraction and HDL3 fraction, and each fraction was reacted with Reagent E described above. Reagent G described below was further added to the reaction solution to perform measurement. In the measurement, 150 µL of Reagent E was added to 2 µL of each fraction, and the reaction was allowed to proceed for 5 minutes with warming, followed by addition of 50 µL of Reagent G to the reaction solution and additional 5 minutes of reaction with warming. The absorbances at a main wavelength of 600 nm and a sub-wavelength of 700 nm were measured.

Reagent G

| BES buffer (pH 7.0) | 100 mmol/L |
|---|---|
| Sodium azide | 0.1% |
| Various surfactants* | 0.01-20.0 w/v % (final concentration: 0.0025-5.0 w/v %) |
| 4-Aminoantipyrine | 4.0 mmol/L |
| Peroxidase | 30 U/mL |

*In cases where two or more surfactants are used in combination, the total concentration is within the range.

The amount of the change in absorbance of each fraction at a unit time after the addition of Reagent G is shown in Table 4. Specific reaction with HDL3 can be seen at the final concentration of 0.025 to 5.0 w/v %, in particular 0.25 to 2.5 w/v % of the polyoxyethylene polycyclic phenyl ethers including polyoxyethylene styrenated phenylether.

TABLE 4

|  | HLB | Final concentration (w/v %) | CM-VLDL | LDL | HDL2 | HDL3 |
|---|---|---|---|---|---|---|
| Polyoxyethylene polycyclic phenyl ether alone | 13.6 | 0.0025 | 1.1 | 0.5 | −0.3 | 1.4 |
|  |  | 0.025 | 0.0 | 0.4 | 2.7 | 8.3 |
|  |  | 0.25 | 1.9 | 2.1 | 15.2 | 119.5 |
|  |  | 0.5 | 1.9 | 2.6 | 18.9 | 126.1 |
|  |  | 0.75 | 2.3 | 3.0 | 21.5 | 125.8 |
|  |  | 1.0 | 2.5 | 3.4 | 23.9 | 126.9 |
|  |  | 1.25 | 2.7 | 3.7 | 26.6 | 127.8 |
|  |  | 2.5 | 2.9 | 5.3 | 38.4 | 126.6 |
|  |  | 5.0 | 3.8 | 11.1 | 58.2 | 131.5 |
| Polyoxyethylene distyrenated phenylethers are mixed | 13.7 | 0.0025 | 0.8 | 0.6 | 1.0 | 0.6 |
|  |  | 0.025 | −0.6 | 0.2 | 2.0 | 8.0 |
|  |  | 0.25 | 1.1 | 3.0 | 12.1 | 104.3 |
|  |  | 0.5 | 2.3 | 5.0 | 16.5 | 121.2 |
|  |  | 0.75 | 2.5 | 5.3 | 20.2 | 126.4 |
|  |  | 1.0 | 3.0 | 6.3 | 23.9 | 125.5 |

TABLE 4-continued

| HLB | Final concentration (w/v %) | CM-VLDL | LDL | HDL2 | HDL3 |
|---|---|---|---|---|---|
|  | 1.25 | 2.5 | 7.8 | 27.6 | 128.1 |
|  | 2.5 | 4.4 | 12.9 | 41.4 | 130.7 |
|  | 5.0 | 5.5 | 22.2 | 63.0 | 133.0 |

(unit: mAbs)

Example 5

A human serum sample was reacted with Reagent A described above, and Reagent H described below was further added to the reaction solution to perform measurement. In the measurement, 150 µL of Reagent A was added to 2 µL of serum, and the reaction was allowed to proceed for 5 minutes with warming, followed by addition of 50 µL of Reagent H to the reaction solution and additional unit time of reaction with warming. The absorbances at a main wavelength of 600 nm and a sub-wavelength of 700 nm were measured to determine HDL3 cholesterol level, and HDL2 cholesterol level was determined by calculation based on the total HDL cholesterol measured otherwise.

Reagent H

| BES buffer (pH 7.0) | 100 mmol/L |
|---|---|
| Sodium azide | 0.1% |
| Polyoxyethylene polycyclic phenyl ether (HLB: 13.6) | 2.0 w/v % |
| 4-Aminoantipyrine | 4.0 mmol/L |
| Peroxidase | 3.5 U/mL |

Figure 2:
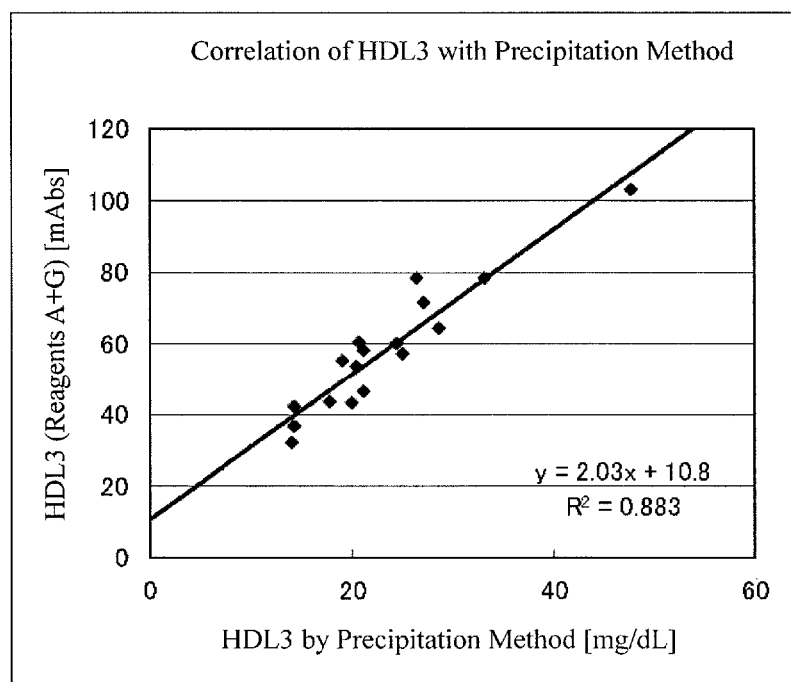
FIG. 2 shows the correlation between HDL3 cholesterol level determined by the present invention and the HDL3 cholesterol level determined by precipitation method, which comparison was carried out in Example 5.
Figure 3:
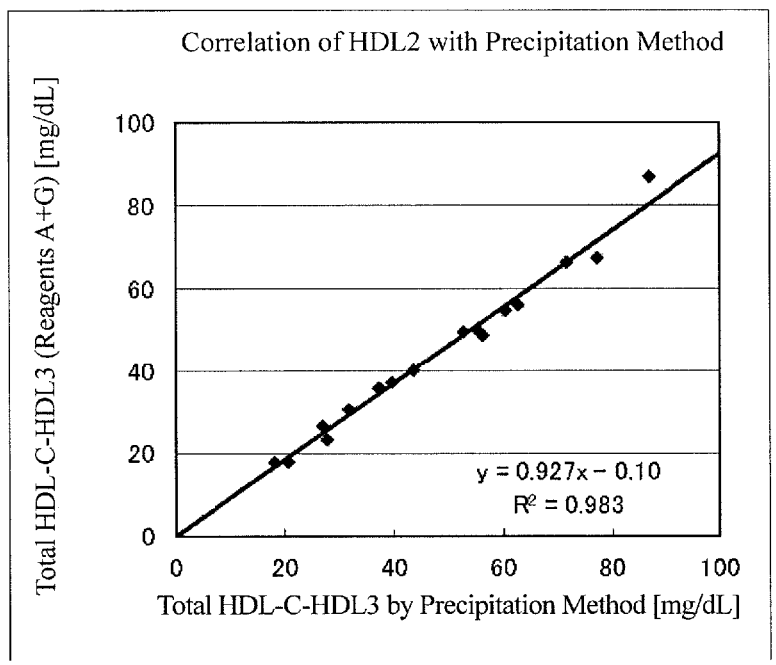
FIG. 3 shows the correlation between HDL2 cholesterol level calculated from HDL3 cholesterol level determined by the present invention and the total HDL cholesterol level, and HDL2 cholesterol level calculated from HDL3 cholesterol level determined by precipitation method and the total cholesterol level, which comparison was carried out in Example 5.

The correlation between HDL3 cholesterol level determined by using Reagent A and Reagent H and HDL3 cholesterol level determined by precipitation method (Patent Document 1) is shown in FIG. 2. The correlation between HDL2 cholesterol level calculated from HDL3 cholesterol level determined by using Reagent A and Reagent H and the total HDL cholesterol level, and HDL2 cholesterol level calculated from HDL3 cholesterol level determined by precipitation method and the total HDL cholesterol level is shown in FIG. 3. For both HDL3 and HDL2, strong correlations can be confirmed between the method of the present invention and the precipitation method.

Example 6

A human serum sample was reacted with Reagent I described below, and Reagent H described above was further added to the reaction solution to perform measurement. In the measurement, 150 µL of Reagent I was added to 2 µL of serum, and the reaction was allowed to proceed for 5 minutes with warming, followed by addition of 50 µL of Reagent E to the reaction solution and additional unit time of reaction with warming. The absorbances at a main wavelength of 600 nm and a sub-wavelength of 700 nm were measured to determine HDL3 cholesterol level, and HDL2 cholesterol level was determined by calculation based on the total HDL cholesterol measured otherwise.

Reagent I

| BES buffer (pH 6.6) | 100 mmol/L |
|---|---|
| HDAOS | 0.56 mmol/L |
| Nonion OT-221 | 0.01 w/v % |
| Catalase | 600 U/mL |
| Cholesterol oxidase | 0.8 U/mL |
| Cholesterol esterase | 2.0 U/mL |
| Sphingomyelinase | 0.5 U/mL |

Figure 4:
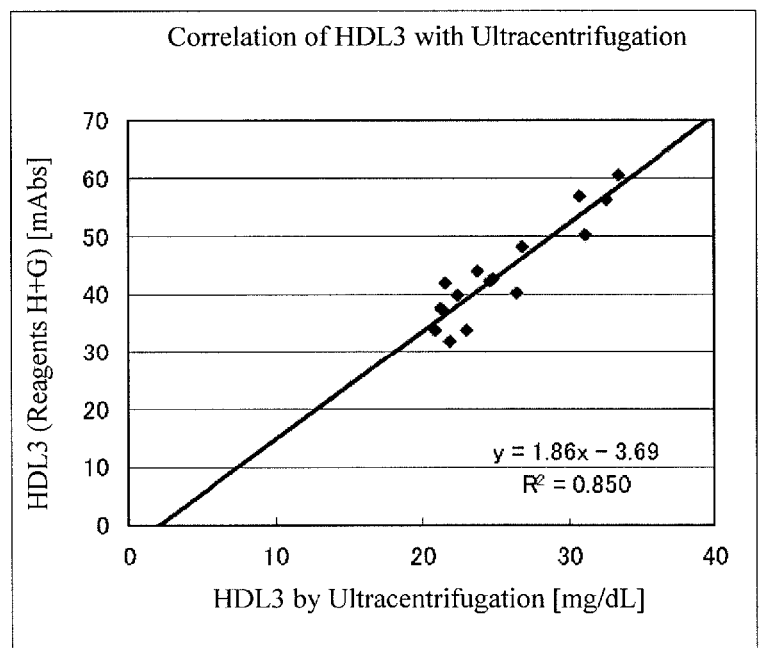
FIG. 4 shows the correlation between HDL3 cholesterol level determined by the present invention and the HDL3 cholesterol level determined by ultracentrifugation, which comparison was carried out in Example 6.
Figure 5:
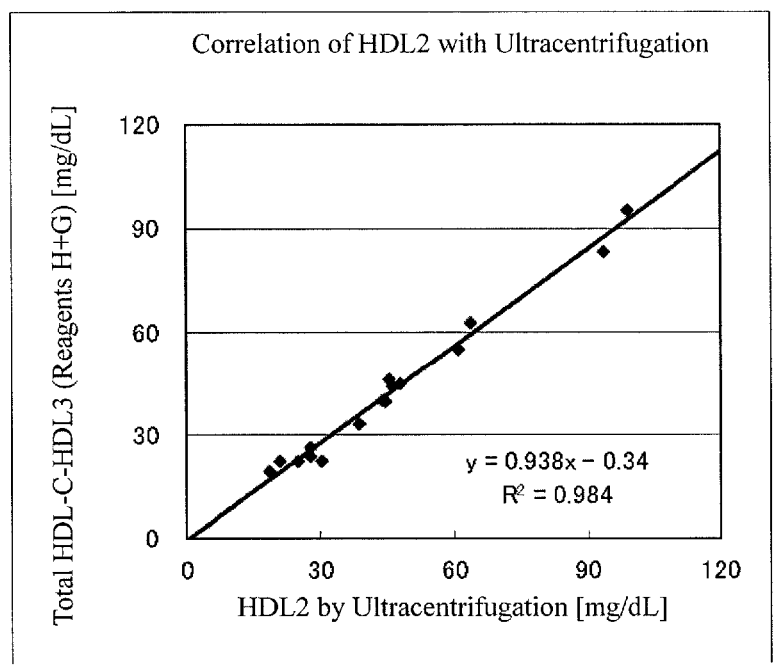
FIG. 5 shows the correlation between HDL2 cholesterol level calculated from HDL3 cholesterol level determined by the present invention and the total HDL cholesterol level, and HDL2 cholesterol level determined by ultracentrifugation, which comparison was carried out in Example 6.

The correlation between HDL3 cholesterol level determined by using Reagent I and Reagent H and HDL3 cholesterol level determined by ultracentrifugation is shown in FIG. 4. The correlation between HDL2 cholesterol level calculated from HDL3 cholesterol level determined by using Reagent I and Reagent H and the total HDL cholesterol level, and HDL2 cholesterol level determined by ultracentrifugation is shown in FIG. 5. For both HDL3 and HDL2, strong correlations can be confirmed between the method of the present invention and the ultracentrifugation.

The invention claimed is:

1. A method for quantifying cholesterol in high-density lipoprotein 3, said method comprising:
    reacting a test sample with two or more surfactants which react specifically with high-density lipoprotein 3; and
    quantifying cholesterol;
    wherein said two or more surfactants are ones selected from the group consisting of polyoxyethylene polycyclic phenyl ethers;
    wherein a total concentration of said surfactants is 0.25 to 1.25 w/v % in terms of the final concentrations;
    wherein the two or more surfactants provide a reaction ratio of high-density lipoprotein 3 to high-density lipoprotein 2 (HDL3/HDL2) of 4.6 to 10.6; and
    wherein the two or more surfactants are combined so as to provide the total hydrophilic-lipophilic balance (HLB) of 13.7 to 14.0 of the combined surfactants.

2. The method according to claim 1, wherein said polyoxyethylene polycyclic phenyl ethers are polyoxyethylene styrenated phenylethers.

3. The method according to claim 2, wherein said polyoxyethylene styrenated phenylethers are polyoxyethylene distyrenated phenylethers.

4. The method according to claim 1, wherein the total concentration of said surfactants is 0.5 to 1.25 w/v % in terms of the final concentrations.

5. The method according to claim 1, wherein the total concentration of said surfactants is 0.25 to 1.0 w/v % in terms of the final concentrations.

* * * * *

UNITED STATES PATENT AND TRADEMARK OFFICE
CERTIFICATE OF CORRECTION

PATENT NO.         : 11,041,869 B2
APPLICATION NO.    : 14/906589
DATED              : June 22, 2021
INVENTOR(S)        : Noriyuki Sato et al.

Page 1 of 1

It is certified that error appears in the above-identified patent and that said Letters Patent is hereby corrected as shown below:

On the Title Page

Column 2 FOREIGN PATENT DOCUMENTS Change:
"EP 0 877 422 A1 12/1998"
To:
-- EP 0 887 422 A1 12/1998 --

Column 2 OTHER PUBLICATIONS Change:
"Ahmadraji, T. and A.J. Killard, "The evolution of selective analyses of HDL and LDL cholesterol in clinical and point of care testing," Analytical Methods (Aug. 7, 2013), vol. 5, No. 15, pp. 3603-3762"
To:
-- Ahmadraji, T. and A.J. Killard, "The evolution of selective analyses of HDL and LDL cholesterol in clinical and point of care testing," Analytical Methods (Aug. 7, 2013), vol. 5, No. 15, pp. 3612-3625 --

Signed and Sealed this
Fifth Day of October, 2021

Drew Hirshfeld
*Performing the Functions and Duties of the
Under Secretary of Commerce for Intellectual Property and
Director of the United States Patent and Trademark Office*